United States Patent [19]

Chu et al.

[11] Patent Number: 4,471,145
[45] Date of Patent: Sep. 11, 1984

[54] PROCESS FOR SYNGAS CONVERSIONS TO LIQUID HYDROCARBON PRODUCTS UTILIZING ZEOLITE BETA

[75] Inventors: Yung-Feng Chu, Cherry Hill; Tai-Sheng Chou, Sewell; Arthur W. Chester, Cherry Hill, all of N.J.

[73] Assignee: Mobil Oil Corporation, New York, N.Y.

[21] Appl. No.: 536,067

[22] Filed: Sep. 26, 1983

Related U.S. Application Data

[63] Continuation-in-part of Ser. No. 445,810, Dec. 1, 9182, Pat. No. 4,423,265.

[51] Int. Cl.³ .............................. C07C 1/04; C07C 1/06
[52] U.S. Cl. .................................. 585/322; 585/315; 585/314; 585/408; 585/469; 585/639; 585/733; 518/719; 208/950; 502/71
[58] Field of Search ............... 585/314, 315, 322, 319, 585/324, 408, 469, 639, 640, 739; 518/701, 702, 703, 704; 208/950

[56] References Cited

U.S. PATENT DOCUMENTS

| 4,041,095 | 8/1977 | Kuo ................................... 208/950 |
| 4,159,995 | 7/1979 | Haag et al. ........................ 518/717 |
| 4,252,736 | 2/1981 | Haag et al. ........................ 518/702 |
| 4,279,830 | 7/1981 | Haag et al. ........................ 208/950 |
| 4,423,265 | 12/1983 | Chu et al. ........................... 585/322 |

Primary Examiner—Delbert E. Gantz
Assistant Examiner—A. Pal
Attorney, Agent, or Firm—Alexander J. McKillop; Michael G. Gilman; Van D. Harrison, Jr.

[57] ABSTRACT

The liquid carrier in a Fischer-Tropsch synthesis slurry reactor system is periodically or continually separated and subjected to cracking and isomerization in the presence of suitable catalysts. The treated carrier is returned to the reactor system and the accumulation of high viscosity paraffin in the reactor slurry is minimized. Suitable catalysts include a mixture of cracking and isomerization catalysts. Zeolite Beta is the novel constituent of the catalyst system.

8 Claims, 2 Drawing Figures

PROCESS FOR SYNGAS CONVERSIONS TO LIQUID HYDROCARBON PRODUCTS UTILIZING ZEOLITE BETA

RELATED APPLICATIONS

This is a continuation-in-part of our copending application Ser. No. 445,810 filed Dec. 1, 1982, now U.S. Pat. No. 4,423,265 which is incorporated herein by reference.

BACKGROUND OF THE INVENTION

Field of the Invention

This invention is concerned with an improved process for converting synthesis gas, i.e. mixtures of gaseous carbon oxides with hydrogen or hydrogen donors, to hydrocarbon mixtures. More specifically this invention is concerned with an improved process wherein the fluidity of the catalyst suspension used in a slurry phase Fischer-Tropsch process is maintained.

Processes are well known for converting coal and other hydrocarbons, such as natural gas, to a gaseous mixture consisting essentially of hydrogen and carbon monoxide and/or dioxide. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, Edited by Kirk-Othmer, Second Edition, Volume 10, pages 353–433 (1966), Interscience Publishers, New York, N.Y. and in the more recent Third Edition, Volume 11, pages 410–446 (1980), John Wiley and Sons, New York, N.Y.

It s also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline zeolite exemplified by ZSM-5 in admixture with a carbon monoxide reduction catalyst. Thus, for example, in U.S. Pat. No. 4,086,262, there is disclosed a process for the conversion of syngas by passing the syngas at elevated temperature over a catalyst which comprises an intimate mixture of a Fischer-Tropsch component and a special type of zeolite such as ZSM-5. This patent points out the the products produced are hydrocarbon mixtures which are useful in the manufacture of heating oil, high octane gasoline, aromatic compounds, and chemical intermediates.

More recently it has been discovered that a highly aromatic or highly olefinic gasoline of enhanced octane number, or a gasoline plus distillate mixture, can be obtained in greater yield from synthesis gas utilizing a selected synthesis gas composition of low $H_2/CO$ ratio in a relatively special Fischer-Tropsch syngas conversion soperation and in a sequentially arranged dual reactor conversion process. Such a process is described in U.S. Pat. No. 4,279,830, which is incorporated herein by reference. The process basically is a two-stage process which consists in the first stage of reacting the syngas mixture in the presence of a special Fischer-Tropsch CO reducing catalyst under preselected conditions. The gaseous product obtained from this first stage syngas conversion is thereafter in the second stage processed in a second reactor with a special crystalline zeolite catalyst of a desired activity to yield a synthetic hydrocarbon product containing a gasoline fraction rich in aromatics.

In conjunction with the Fischer-Tropsch process, there has been developed more recently the slurried catalyst reactor system. This can otherwise be described as a suspended Fischer-Tropsch catalyst in a liquid medium suitable for the purpose of converting syngas to hydrocarbon products. The slurried ctalyst reactor system is discussed in U.S. Pat. No. 4,252,736 which is incorporated herein by reference. This particular reactor system is also discussed extensively in the article, "Fischer-Tropsch Synthesis in Slurry Phase", M. D. Schlesinger et al, Industrial Engineering Chemistry, Volume 43, Number 6, page 1474 (1951). Basically the slurried catalyst process constitutes a process in which a finely divided iron catalyst suspended in oil is circulated by natural convection through a reactor in the presence of synthesis gas. U.S. Pat. No. 4,252,736 discloses a process in which synthesis gas is first bubbled through a column of Fischer-Tropsch catalysts suspended in oil. The effluent is then flowed through a bed of zeolite (ZSM-5) and hydrocarbons boiling in the range of gasoline and distillate fuels are recovered from this second effluent.

In any process using a slurried catalyst to convert the syngas to higher molecular weight hydrocarbons, it has been noted that with the passage of time the slurry of catalyst becomes increasingly viscous until the slurry approaches gellation at reaction conditions. When this condition prevails, the process must be discontinued and at least a portion of the slurry must be replaced by a more fluid suspended agent. This tendency of the catalyst slurry to become thicker is thought to result from the formation and accumulation of heavier hydrocarbon waxes of $C_{30}+$ comosition. The formation of these heavier hydrocarbons results in loss of product as well as loss of production time. A primary object of this invention accordingly is to prevent the buildup of heavier hydrocarbons in the catalyst slurry in a Fischer-Tropsch process. Zeolite Beta and ZSM-45 are the novel constituents of the catalyst system.

DESCRIPTION OF THE DRAWING

In the accompanying drawing.

SUMMARY OF THE INVENTION

Figure 1:
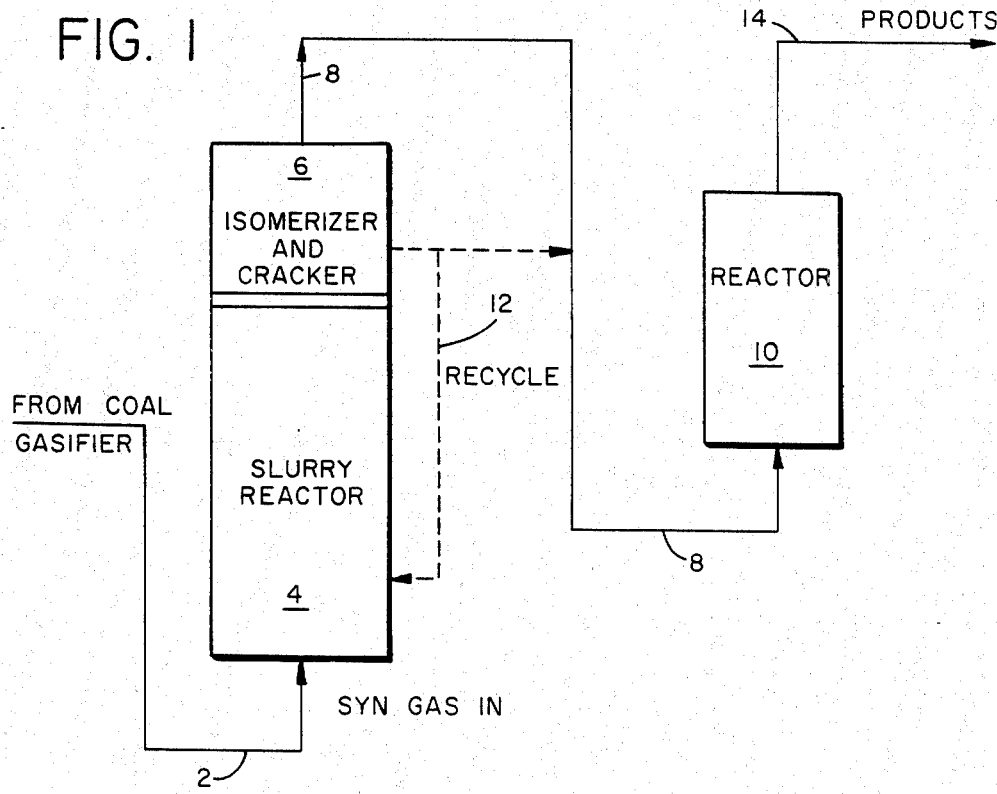
FIG. 1 is a flow sheet for one embodiment of the invention.

Briefly stated our invention in a broad sense comprises either periodically or continually removing a portion of the Fischer-Tropsch catalyst slurry in a Fischer-Tropsch synthesis slurry reactor system, separating the catalyst from the liquid carrier, subjecting the liquid carrier to isomerization and cracking and returning a portion of the cracked and isomerized product to the reactor zone while diverting the remainder of the product to the effluent stream from the synthesis reactor. Zeolite Beta and zeolite ZSM-45 are novel constituents, either of which can be used in the catalyst system.

DESCRIPTION OF THE INVENTION

The slurried catalyst reactor system, otherwise identified as a Fischer-Tropsch catalyst suspended in a liquid medium suitable for the purpose of converting syngas to hydrocarbon products has been the subject of numerous patents. Early patents on the subject are U.S. Pat. Nos. 2,438,029; 2,680,126; 2,775,607; 2,852,350 and numerous others.

In the aspect of this invention directed to converting relatively low-ratio syngas (1/1 or less $H_2/CO$ ratio), it is essential that the CO reducing catalyst used include water gas shift activity to be characterized so that steam formed in the Fischer-Tropsch operation by converting the low ratio syngas will react with charged CO to form $H_2$. Examples of CO reducing catalysts having shift activity are iron alone, or iron, cobalt, ruthenium provided with an added shift catalyst component. Shift catalysts suitable for the purpose include those containing the elements Fe, Cr, Zn or Cu. It is also contemplated charging some steam with syngas of 0.7 $H_2/CO$ ratio or less.

At this point in the conversion of synthesis gas to gasoline and distillate, our invention becomes important. As vapors and liquid product is removed from the liquid in the slurry reaction zone. It tends to increase in viscosity until the system requires shutdown or dilution of the slurry with compatible hydrocarbons. In our invention, a portion of the slurry is withdrawn, hydrocarbons separated from the Fischer-Tropsch synthesis catalyst and is then converted in the cracking and isomerization zone where it is subjected to cracking and isomerizing into a ligher and less waxy hydrocarbon fraction. Separation of Fischer-Tropsch synthesis catalyst from the carrier liquid can be effected by filtration and/or magnetic separation. Separation can be performed either in a zone immediately adjacent to the reactor zone or physically removed therefrom. The cracking and isomerization operation is carried out using preferably a mixture of cracking and isomerization catalysts. Preferred conditions for the cracking and isomerization operation are between 400° F. and 800° F. and a pressure of 0 to 1000 psig in the cracking zone. The resultant product is then diverted into a recycle fraction which is returned to the Fischer-Tropsch reactor and the another fraction which is returned to the effluent stream from the Fischer-Tropsch reactor and processed further in the second stage of the reactor to provide a product rich in gasoline or diesel hydrocarbons.

In FIG. 1 synthesis gas is introduced into the reactor 4 through line 2. Reactor 4 contains a slurry of a Fischer-Tropsch catalyst in oil. In the reactor 4 a synthesis gas is converted to a mixture of oxygenates and hydrocarbons including some high molecular weight products which, because of their low volatility accumulate in the liquid slurry. A portion of the slurry is filtered free of suspended catalyst at the top of the reactor and is then passed into cracking and isomerizing zone 6 where it is contacted with a cracking catalyst. A portion of the cracked and isomerized product is then flowed along with the remainder of the product from the top of the zone 6 into line 8 and is then converted in unit 10 to aromatic and other hydrocarbon products. In unit 10 the product from line 8 is contacted with a catalyst, preferably a zeolite catalyst exemplified by ZSM-5 where it is further converted to gasoline and diesel boiling range hydrocarbons. The effluent from reactor 10 can then be further refined into gasoline and distillate materials.

The remaining portion of the cracked and isomerized product is recycled to the slurry reactor via line 12. Because the cracked and isomerized products have a substantially reduced viscosity due to their lower molecular weight, the viscosity of the slurry reactor liquid is reduced.

Figure 2:
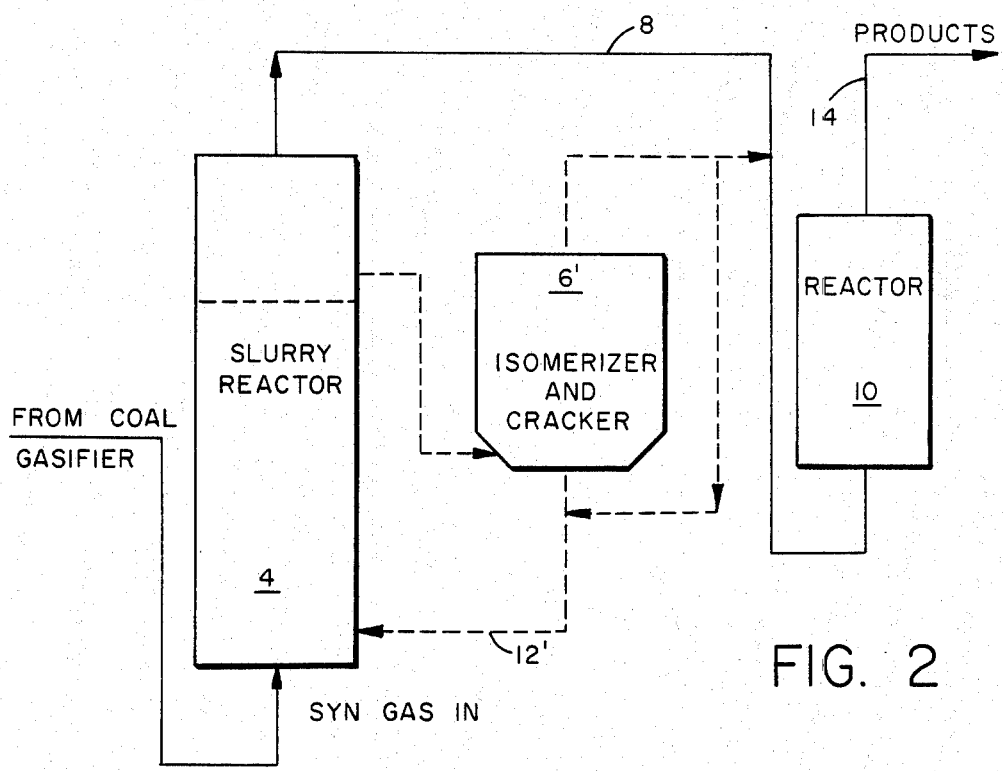
FIG. 2 is a flow sheet depicting a second embodiment.

In FIG. 2 the process is essentially the same except that the cracking and isomerizing zone 6' is a separate unit and the cracked isomerized product is partially recycled to the Fischer-Tropsch reactor 4 and to the second stage 10 of the process.

In the cracking and isomerization zone 6 or 6' it is preferred that a mixture of cracking and isomerization catalysts be used. The cracking coponent preferably is a zeolite selected from the group consisting of small pore zeolites, such as ZSM-5, and large pore zeolites, such as Zeolite X or Y, and zeolite-Beta and zeolite ZSM-45. The isomerization component can be Group VIII metals such as platinum or palladium deposited on alumina or on a zeolite preferably ZSM-5 or zeolite-Beta. Preferred conditions are a temperature of 400° F. to 800° F., a pressure of 0 to 1000 psig and a space velocity of 0.1 to 20.

The catalyst utilized in reactor 10 preferably is a zeolite exemplified by ZSM-5 and preferably is in the form of a fixed bed.

ZSM-5 zeolites are exemplified by ZSM-5, ZSM-11, ZSM-12, ZSM-23, ZSM-35, ZSM-38, ZSM-48 and other similar zeolite materials.

ZSM-5 is described in greater detail in U.S. Pat. No. 3,702,886 and No. Re. 29, 948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern disclosed therein, is incorporated herein by reference.

ZSM-12 is described in U.S. Pat. No. 3,832,449. That description, and in particular the X-ray diffraction pattern disclosed therein, is incoporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,106,245. The description of that zeolite, and particularly the X-ray diffraction pattern thereof, is incorporated herein by reference.

ZSM38 is more particularly described in U.S. Pat. No. 4,046,859. The description of that zeolite, and particularly the specified X-ray diffraction pattern thereof, is incorporated herein by reference.

ZSM-48 is more particularly described in U.S. Pat. Nos. 4,375,573 and 4,397,827, the entire contents of both of which are incorporated herein by reference.

Zeolite Beta is described in U.S. Pat. No. 3,308,069. The description, and particularly the X-ray diffraction pattern disclosed therein, are both incorporated herein by reference.

Zeolite ZSM-45 is described in pending application Ser. Nos. 425,019 and 425,018, both filed on Sept. 27, 1982. Both of these applications are incorporated herein by reference.

In a typical and preferred embodiment of the process of this invention, the feedstream of oxygenates and hydrocarbons in line 8 is introduced into the reaction zone 10 at a temperature within the range of 400° F. and about 950° F., a pressure within the range of $1 \times 10^5$ pascal (0 to 1000 psig), and a WHSV of 0.1 to 20.

Preferred temperatures in the reaction zone 10 fall within the range of 400° F. to 900° F. and preferred pressures fall within the range of $1 \times 10$ to $15 \times 10^5$ pascal (0 to 800 psig). A preferred WHSV is between 0.2 and 5. These latter ranges of temperature, pressure and WHSV are believed to embody the best mode of conducting the process of this invention.

What is claimed is:

1. A process for converting synthesis gas to liquid hydrocarbons having a boiling range within that of gasoline and distillate comprising the steps of:
    (a) charging said synthesis gas to a Fischer-Tropsch synthesis conversion zone comprising a catalyst providing CO reducing characteristics in a single form or a combination of catalyst particles in direct contact with a suspending liquid medium;
    (b) separating at least a fraction of said suspending liquid medium containing dissolved heavier hydrocarbons from said catalyst particles;
    (c) contacting said separated suspending medium containing heavier hydrocarbons in a cracking zone with a cracking and isomerization catalyst comprising zeolite Beta under conditions effective to crack and isomerize at least a portion of said heavier hydrocarbons to lighter hydrocarbons;
    (d) separating the resultant product stream of (c) into two streams;
    (e) removing an effluent stream from said conversion zone of (a) to a second reaction zone containing a crystalline zeolite catalyst;
    (f) returning one of said streams of (d) to said effluent stream from zone (a);
    (g) returning the remaining stream of (d) to said conversion zone of (a); and
    (h) contacting said effluent stream from said conversion zone of (a) with a crystalline zeolite to convert the product of said Fischer-Tropsch synthesis gas conversion to hydrocarbons boiling within the range of distillate and gasoline.

2. The process of claim 1 wherein said zeolite Beta has deposited thereon a metal selected from the group consisting of platinum and palladium.

3. The process of claim 1 wherein the cracking zone of (c) is contiguous to said slurry reactor zone.

4. The process of claim 1 wherein the cracking zone of (c) is separated from said Fischer-Tropsch reaction zone.

5. The process of claim 1 wherein the contacting of said suspending medium with zeolite Beta is conducted at a temperature between about 400° F. and about 800° F.

6. The process of claim 1 wherein the contacting of said suspending medium is conducted at a pressure between about 0 and about 1000 psig.

7. The process of claim 1 wherein the contacting of said suspending medium is conducted at a liquid hourly space velocity of between about 0.1 and about 20.

8. The process of claim 1 wherein said isomerization catalyst is a Group VIII metal deposited on zeolite Beta.

* * * * *